April 13, 1971 H. A. JOHNSON, JR., ET AL Plant Pat. 3,043
STRAWBERRY PLANT
Filed June 11, 1969
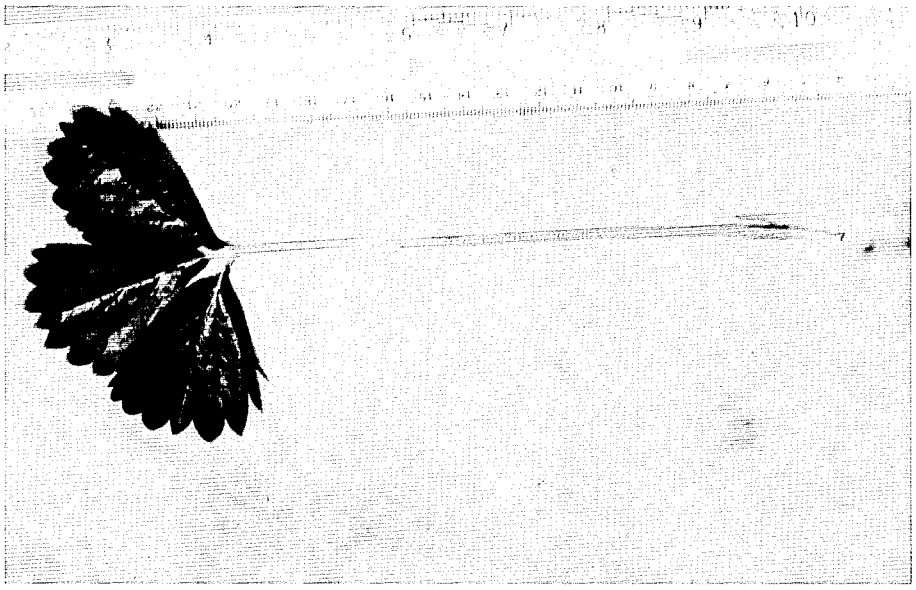
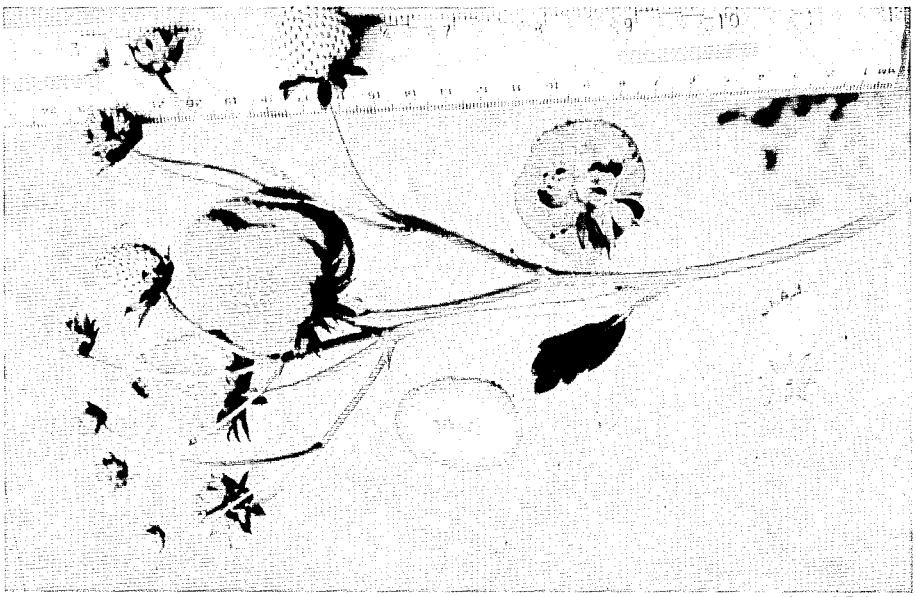
INVENTORS
HAROLD A. JOHNSON, JR.
HAROLD E. THOMAS
BY Townsend and Townsend
ATTORNEYS United States Patent Office Plant Pat. 3,043
Patented Apr. 13, 1971

3,043
STRAWBERRY PLANT

Harold A. Johnson, Jr., and Harold E. Thomas, Watsonville, Calif., assignors to Driscoll Strawberry Associates, Inc., Watsonville, Calif.

Filed June 11, 1969, Ser. No. 832,511
Int. Cl. A01h 5/03
U.S. Cl. Plt.—49 1 Claim This invention relates to a new and distinct variety of strawberry plant which is the result of a cross of the unpatented everbearing variety known as The Strawberry Institute of California selection No. F121.7 and the variety disclosed in the Goldsmith Pat. No. 1,735 issued July 29, 1958.

The seedlings resulting from the aforementioned cross were grown and asexually multiplied in Shasta county, Calif. and tested in the fruiting beds on the property of growers of the Driscoll Strawberry Associates, Inc. Clones of the seedlings were also held at the Propagation Nursery in Shasta county. One plant was selected from the aforementioned group of seedlings and further asexual reproduction was performed in the Shasta county nursery of Driscoll Strawberry Associates, Inc. Tests followed in various parts of California during intervening seasons on various properties of grower members of the Driscoll Strawberry Associates, Inc. These tests indicated the merit of the novel plant and resulted in its selection as a promising test variety.

Parts of a plant of the new variety, typical in size, shape and color are pictured in the accompanying drawing in which two ripe berries are shown. To exemplify flesh color and core cavity, a third and fourth berry is shown in cross section. The inflorescence pictured is typical of branching and relative size on or about the middle of July during which the leaf shown is also typical in appearance and size. The flower shown is a typical secondary flower.

The novel plant is small to medium in size, but vigorous, becoming larger by the end of the first season and considerably larger the second year. Many crowns can develop. It is an everbearing variety in that it can be planted during the spring or winter while yielding a crop the same growing year. This variety produces small fruit from the crown crop, but the first main crop has primaries that are large and showy. The crop can usually be harvested during the last days of May if planting takes place during late January or early February. The first main crop has the largest fruits.

The novel plant of the present invention distinguishes over other varieties by its flowers, fruit and plant characteristics. In general, the plant does not become as large as the Goldsmith variety and produces more but smaller leaves per plant. The petioles vary in length from very long to very short. Even though there are many leaves per plant, they are not dense. The leaflets point upward and are lighter in color than the leaflets of the Goldsmith variety. The petioles become reddish green in color to give them a distinct appearance. The plant is susceptible to Leaf Spot. The leaflet diameter is smaller than that of the Goldsmith variety and the leaflet margins have deep serrations with a sharp apex. Bracts are often found on the petioles.

The inflorescences of this new variety are as long as those of the Goldsmith variety but are more abundant and have a more delicate peduncle and pedicel. Each inflorescence produces fewer berries than the Goldsmith variety. The pedicel diameter of each is less than that of Goldsmith. The primary peduncle increases in length as the season progresses. The pedicel holding primary berries of most inflorescences originates mainly from one of the peduncles, as is pictured in the illustrations, but occasionally originates from the axial formed by the union of the peduncles. There are usually just two secondary peduncles per inflorescence rather than three as most commonly occurs in the Goldsmith variety. The flowers are noticeably visible above the plant, especially during the first year of production. The pubescence on tertiary pedicles is equal to that found on the Goldsmith variety, except that the novel plant sometimes produces hair that is slightly more crinkled in appearance.

The primary berries are large and distinct, often becoming 40 mm. in length and they are round wedged in outline with longitudinal furrows extending the full length of the berry. Secondary berries become smoother and vary from wedged to round conic in outline as described in the U.S.D.A. Bulletin No. 1043. There is a sharp drop in size between primary, secondary and tertiary fruits. In comparison with berries of the Goldsmith variety the surface is glossier and darker, but the flesh is lighter with a smaller, more solid core. It has a higher sugar content and better dessert qualities than Goldsmith berries. The seeds become quite dark on the exposed side of the fruit and are held on or slightly below the fruit surface. The epidermis of primary berries is firm, but secondaries and tertiaries are often weaker and more vulnerable to picking and shipping damage than Goldsmith berries. There is generally no particular aroma peculiar to the flesh of this variety.

The calyx is smaller in diameter than in the Goldsmith variety and, except for primary fruit, the sepals do not overlap and generally are elliptical in outline. This new variety is an abundant runner producer both in the fruiting beds and at the nursery. It is equal or superior to the Goldsmith variety in its resistance to the Two-Spotted Mite and Powdery Mildew. It is susceptible to Verticillium Wilt, Cyclamen Mite and Red Stele. It is quite susceptible to thrips which damage the fruit and cause a bronzed and scarred appearance. As a seedling this variety withstood the natural virus invasion of the various components found in central California without losing its ability to produce.

The varietal characteristics of the novel plant, described below in detail, were observed during the first fruiting season. Observations were made in the Watsonville area of California which is a cool coastal area near the Pacific Ocean. The color terminology is in accordance with Ridgway's Color Standards and Nomenclature (1912 Edition).

*Plants.*—Small to medium in size, becoming denser the second year with a strong root system.

*Leaves.*—Are small to medium in size. The central leaflet is mostly 5 to 7 cm. in diameter. The length is greater than the width. Leaflet margins are cupped upward especially at the base near the petiolule. The leaf serrations are deep and acute at the apex, becoming noticeably pointed. The petioles vary from short to long in length with bracts often present. The color of the upper leaflet side at Watsonville in July is Yew Green, Plate XXXI.

*Runners.*—Are abundant and vigorous at the nursery and in the fruiting beds.

*Inflorescence.*—Is medium to long in length with usually only two secondary peduncles per inflorescence. The pedicel holding the primary berry usualy originates from a secondary peduncle, but may also originate from the axil formed by the union of peduncles. Anthers produce an abundance of pollen even under cold, wet and windy conditions. Flowers are conspicuously visible above the plant. Hair on the tertiary pedicels 20 mm. below the flower lays against and is parallel with the pedicel.

*Fruit.*—Crown crop berries are small but primaries from first main crop are large, glossy and attractive, 35 to 45 mm. in length with the width often greater than the length. Secondaries and tertiaries are considerably smaller than primaries. Primaries are irregularly wedged to conic with longitudinal furrows extending the length of the fruit.

Secondaries and tertiaries are not furrowed and tend to be round conic to short wedge. Skin and flesh are firm, the core is small and the berry has a high dessert quality. The outside color of the fruit is a glossy and dark Oxblood Red, Plate 1. The flesh color is White to Nople Red, Plate 1. The color of the center core is Rose Doree, Plate 1.

*Calyx.*—Small in diameter, mostly 28 to 34 mm. Sepals overlap on primaries only, and mostly elliptical in outline with serrations present on some.

We claim:

1. The new and distinct variety of strawberry plant herein described and illustrated, and identified by the characteristics enumerated above.

No references cited.

ROBERT V. BAGWILL, Primary Examiner